United States Patent [19]

Ali et al.

[11] 4,292,305

[45] Sep. 29, 1981

[54] ANTIALLERGIC IMIDODISULFAMIDES

[75] Inventors: Fadia E. Ali, Cherry Hill; Robert D. Krell, Medford, both of N.J.; Kenneth M. Snader, Hatboro, Pa.

[73] Assignee: SmithKline Corporation, Philadelphia, Pa.

[21] Appl. No.: 121,066

[22] Filed: Feb. 13, 1980

[51] Int. Cl.$^3$ .................. A61K 31/135; C07C 143/72; C07C 143/84

[52] U.S. Cl. ...................................... 424/45; 424/330; 564/79

[58] Field of Search ............. 424/45, 330; 260/556 N, 260/556 SN

[56] References Cited

U.S. PATENT DOCUMENTS 3,860,723  1/1975  Baile et al. ........................... 424/321

OTHER PUBLICATIONS

Chemical Abstracts 52:13664a (1958).
Chemical Abstracts 69:2166g (1968).
Chemical Abstracts 60:2800h (1964).
Chemical Abstracts 68:12390u (1968).
Chemical Abstracts 76:87545x (1972).
Chemical Abstracts 88:6264c (1978).
Derwent's Farmdoc #11,875 (4-1964).

*Primary Examiner*—Leonard Schenkman
*Attorney, Agent, or Firm*—Joseph F. DiPrima; Richard D. Foggio; Alan D. Lourie

[57] ABSTRACT

Imidodisulfamide derivatives useful in the treatment of allergic conditions are prepared by reaction of an appropriately substituted primary amine and bis(chlorosulfonyl) imide in the presence of a tertiary amine.

14 Claims, No Drawings

ANTIALLERGIC IMIDODISULFAMIDES

This invention relates to novel imidodisulfamides which are useful as end-organ antagonists of slow reacting substance of anaphylaxis. This substance (SRS-A) has been suggested to be an important mediator of anaphylaxis in human asthma. By antagonizing the effects of this or other pharmacologically active mediators at the end-organ, bronchial smooth muscle, the compounds of this invention are valuable in the treatment of allergic diseases such as asthma.

The imidodisulfamide compounds of this invention are represented by the following general structural formula:

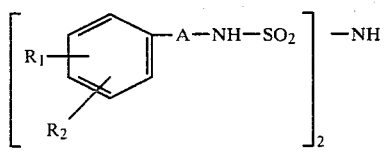

FORMULA I wherein:

A represents a single valence bond (—), an alkylene chain —$(CH_2)_n$— in which n is a positive integer 2, 3, 4 or 6, a branched alkylene chain of from 2 to 4 carbon atoms, or phenylmethylene

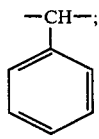

$R_1$ represents hydrogen, 3- or 4-bromo, 3- or 4-chloro, or 3- or 4-trifluoromethyl; and $R_2$ represents hydrogen, with the proviso that when n is 2, $R_1$ is 4-chloro, 4-bromo, 4-methoxy or 3-trifluoromethyl and $R_2$ is hydrogen or together with $R_1$ in adjacent positions forms either a 3,4-dichloro substitution or a fused benzo ring, and further with the proviso that when A is a single valence bond $R_1$ is not hydrogen or 4-chloro.

Particular compounds of this invention represented by formula I above are when A is an alkylene chain, $R_1$ is hydrogen, 3-bromo, 3-chloro or 4-chloro, and $R_2$ is hydrogen.

Alkali metal salts of the compounds of formula I, for example sodium or potassium salts, are obtainable by treatment with the appropriate alkali metal alkoxide, for example methoxide, in an alkanol solvent such as methanol.

The compounds of formula I are conveniently prepared as shown in the following scheme:

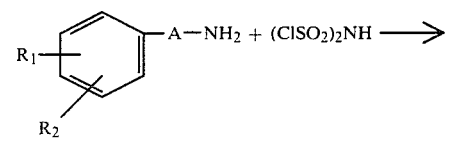

-continued

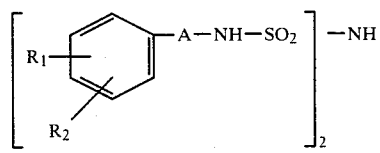

in which A, $R_1$ and $R_2$ are as described above. Thus, the appropriately substituted primary amine is reacted with bis(chlorosulfonyl)imide in the presence of a tertiary amine, for example triethylamine, and in an inert organic solvent, for example acetonitrile, at a temperature which is first below 0° C. and then at from about 0° C. to ambient temperature for at least 12 hours. Treatment of the reaction product with dilute mineral acid affords the imidodisulfamide compound.

The primary amine starting materials used as above are obtained by standard reactions well known in the art. Bis(chlorosulfonyl)imide is prepared from chlorosulfonic acid and chlorosulfonylisocyanate.

The SRS-A antagonist activity of the compounds of this invention is measured by the ability of the active medicament to inhibit SRS-A induced contraction of guinea pig ileum. In this test system, sections of ileum are resected from guinea pigs and placed in 5 ml. tissue baths containing a modified Tyrode's solution. One end of the tissue is fixed to a glass tissue holder, the other is connected to a force-displacement transducer and the tissue is placed under a tension of 500 mg. Isometric tissue contractions are recorded on a six channel polygraph. Baths are constantly aerated with 95% $O_2$–5% $CO_2$. After a 20 minute stabilization period a concentration of the appropriate agonist which provides a contraction height of 60–80% of the maximum obtainable to that agonist (as determined from full sequential concentration—response curves in separate experiments) is added to the tissue bath and the response recorded. The procedure is repeated until reproducible responses are obtained. For most agonists, two applications in rapid succession, followed 15 minutes later by a third, is sufficient to establish reproducibility. Experimental tissues are incubated with the selected concentration of the test compounds for 15 minutes. Experimental and control tissues are subjected to 5 bath changes during the incubation interval. Changes in bath fluid during the incubation period are helpful in insuring the reproducibility of tissue responses to the agonist. The same concentration of the agonist is reapplied in the presence of the test compound and the response registered and compared with controls. Percent inhibition produced by the test compound is calculated by substracting the mean percentage change in control tissue from the mean percentage change in tissues exposed to the test compound. Additional compounds are then evaluated as long as the tissue remains reproducibly responsive to the agonist. Six tissues obtained from 6 animals are used simultaneously—3 controls and 3 experimental.

The compounds of this invention tested at concentrations of from $5 \times 10^{-5}$M to $1 \times 10^{-5}$M produce marked antagonism of partially purified slow reacting substance of anaphylaxis obtained from guinea pig lung. The agonist is employed at a concentration of 40 µg/ml. For example, 1,5-di-(4-bromophenyl)-imidodisulfamide produced 47% antagonism of SRS-A at $5 \times 10^{-5}$M; 1,5-di-(4-chlorophenethyl)imidodisulfamide produced 64% antagonism of SRS-A at $5 \times 10^5$M; and 1,5-di-(4-phenylbutyl)-imidodisulfamide produced 40% antagonism of SRS-A at $1 \times 10^{-5}$M.

The specificity of the antagonist activity of the compounds of this invention is demonstrated by relatively low levels of antagonism toward agonists such as potassium chloride, serotonin, histamine and the prostaglandins $F_{2\alpha}$ and $E_2$.

The compounds of this invention may be administered in conventional pharmaceutical compositions comprising an appropriate amount of a compound of formula I in association with a pharmaceutical carrier of diluent. The nature of the composition and the pharmaceutical carrier or diluent will of course depend upon the intended route of administration, i.e. parenterally or by inhalation. Usually a compound is administered to an animal or human subject in a composition comprising an amount sufficient to produce an inhibition of the symptoms of an allergic response. When employed in this manner, the dosage of the compositions is such that from 0.5 mg. to 500 mg. of active ingredient are administered at each administration. For convenience equal doses will be administered 1 to 4 times daily with the daily dosage regimen being selected from about 0.5 mg. to about 2000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g. lactose, for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

For parenteral administration the pharmaceutical composition will be in the form of a sterile injectable liquid such as an ampul or an aqueous or nonaqueous liquid suspension. Exemplary of liquid carriers are peanut oil, olive oil or water.

The pharmaceutical preparations thus described are made following the conventional techniques of the pharmaceutical chemist as appropriate to the desired end product.

Included within the scope of this invention is the method of inhibiting the symptoms of an allergic response resulting from a mediator release which comprises administering to an animal or human subject a therapeutically effective amount for producing said inhibition of a compound of formula I, preferably in the form of a pharmaceutical composition. The administration may be carried out in dosage units at suitable intervals or in single doses as needed. Usually the method of this invention will be practiced when relief of allergic symptoms is specifically required, however, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

The following examples illustrate the preparation of compounds of formula I and their incorporation into pharmaceutical compositions and as such are not to be considered as limiting the invention set forth in the claims appended hereto.

EXAMPLE 1

A mixture of 166 g. (1.42 mole) of chlorosulfonic acid and 202 g. (1.42 mole) of chlorosulfonylisocyanate was heated under reflux (110° C.) in an oil bath until the evolution of carbon dioxide ceased. The crude product was distilled in vacuo to yield bis(chlorosulfonyl)imide, b.p., (1.5 mm.) 100° C.

To 8.56 g. (0.04 mole) of bis(chlorosulfonyl)imide in 20 ml. of dry acetonitrile at $-40°$ C. was added dropwise 12.1 g. (0.12 mole) of triethylamine (sodium hydroxide-dried). The mixture was warmed to 0° C. and 15.48 g. (0.09 mole) of 3-bromoaniline in 20 ml. of dry acetonitrile was added slowly. The reaction mixture was stirred at room temperature for 12 hours. The hydrochloride salt of triethylamine was filtered and the filtrate was concentrated to dryness under reduced pressure. The residual oil was treated with ethanol/dilute hydrochloric acid to give a solid which was recrystallized from ethanol to furnish 1,5-di-(3-bromophenyl)-imidodisulfamide, m.p. 178°–179° C.

| Analysis | C | H | N | S | Halogen |
|---|---|---|---|---|---|
| Calculated: | 29.71 | 2.29 | 8.66 | 13.22 | 32.94 |
| Found: | 29.87 | 2.36 | 8.75 | 13.30 | 32.66 |

Similarly, reacting 2.75 g. (0.0129 mole) of bis(chlorosulfonyl)imide, 5.38 ml. (0.0386 mole) of triethylamine and 5.0 g. (0.029 mole) of 4-bromoaniline as described above gave 1,5-di-(4-bromophenyl)-imidodisulfamide, m.p. 215°–222° C. (sodium salt).

| Analysis | C | H | N |
|---|---|---|---|
| Calculated: | 27.42 | 2.28 | 8.00 |
| Found: | 27.52 | 2.19 | 8.43 |

EXAMPLE 2

To 17.12 g. (0.08 mole) of bis(chlorosulfonyl)imide in 40 ml. of dry acetonitrile at $-40°$ C. was added dropwise 16.12 g. (0.16 mole) of dry triethylamine. The mixture was warmed to 0° C., 20.4 g. (0.16 mole) of 3-chloroaniline in 40 ml. of dry acetonitrile was added slowly and the resultant mixture was stirred at room temperature for 12 hours. The reaction mixture was filtered and the filtrate was concentrated. The residue was dissolved in methanol, acidified with dilute hydrochloric acid and the resulting solid was recrystallized from aqueous methanol to give 1,5-di-(3-chlorophenyl)-imidodisulfamide, m.p. 164.5°–166° C.

| Analysis | C | H | N | S | Halogen |
|---|---|---|---|---|---|
| Calculated: | 35.96 | 2.89 | 10.49 | 16.00 | 17.69 |
| Found: | 36.08 | 3.19 | 10.68 | 15.78 | 17.78 |

Following the procedures of Examples 1 and 2, the appropriately substituted primary amines were reacted with bis(chlorosulfonyl)imide in the presence of triethylamine to give the imidodisulfamide product as indicated in the following table:

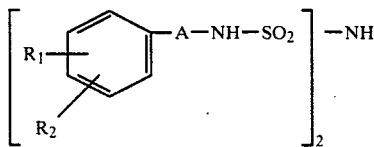

| Example # | $R_1$ | $R_2$ | A | M.P. °C. | ANALYSIS Calculated C | H | N | S | Halo | Found C | H | N | S | Halo |
|---|---|---|---|---|---|---|---|---|---|---|---|---|---|---|
| 3 | 3-$CF_3$ | H | — | 179–80 | 36.29 | 2.39 | 9.07 | 13.84 | 24.60 | 36.57 | 2.51 | 9.16 | 14.06 | 24.32 |
| 4 | 4-$CF_3$ | H | — | 148.5–9 | 36.29 | 2.39 | 9.07 | 13.84 | | 35.96 | 2.55 | 9.07 | 13.98 | |
| 5 | 4-Cl | H | $(CH_2)_2$ | 148–9 | 42.48 | 4.23 | 9.29 | 14.18 | 15.67 | 42.22 | 3.94 | 9.29 | 13.96 | 15.30 |
| 6 | 4-Br | H | $(CH_2)_2$ | 152–4 | 35.50 | 3.54 | 7.76 | | | 35.43 | 3.39 | 7.97 | | |
| 7 | 3-$CF_3$ | H | $(CH_2)_2$ | 139–40 | 41.62 | 3.61 | 8.09 | | | 41.49 | 3.72 | 8.19 | | |
| 8 | 4-$OCH_3$ | H | $(CH_2)_2$ | 152–3 | 48.74 | 5.68 | 9.47 | 14.46 | | 48.74 | 5.86 | 9.41 | 14.17 | |
| 9 | 4-Cl | 3-Cl | $(CH_2)_2$ | 110–11 | 36.88 | 3.29 | 8.06 | | | 37.01 | 3.56 | 7.57 | | |
| 10 | 2,3-benzo | | $(CH_2)_2$ | 168–70 | 58.52 | 5.32 | 8.53 | 13.02 | | 58.38 | 5.33 | 8.22 | 12.97 | |
| 11 | H | H | $CH(CH_3)CH_2$ | 80–85 | 52.53 | 6.12 | 10.21 | 15.58 | | 52.59 | 6.28 | 10.19 | 15.30 | |
| 12 | H | H | $(CH_2)_2CH(CH_3)$ | 143–50 | 54.65 | 6.65 | 9.56 | 14.59 | | 54.58 | 6.73 | 9.48 | 14.45 | |
| 13 | H | H | $CH(C_6H_5)$ | 198–200 | 61.52 | 4.96 | 8.28 | 12.63 | | 61.26 | 5.09 | 8.26 | 12.47 | |
| 14 | 4-Cl | H | $CH(CH_3)CH_2$ | 146–8 | 45.00 | 4.83 | 8.75 | 13.32 | 14.76 | 45.36 | 4.98 | 8.75 | 13.16 | 14.38 |
| 15 | 4-Cl | H | $CH(CH_3)$ | 151–3 | 42.48 | 4.23 | 9.29 | 14.18 | 15.67 | 42.38 | 4.32 | 9.31 | 14.20 | 15.88 |
| 16 | H | H | $(CH_2)_3$ | 174–5 | 52.53 | 6.12 | 10.21 | 15.58 | | 52.61 | 6.13 | 10.24 | 15.38 | |
| 17 | H | H | $(CH_2)_4$ | 133–4 | 54.65 | 6.65 | 9.56 | 14.59 | | 54.59 | 6.54 | 9.60 | 14.34 | |
| 18 | H | H | $(CH_2)_6$ | 134–5 | 58.15 | 7.52 | 8.48 | 12.94 | | 58.10 | 7.45 | 8.54 | 13.12 | |
| 19 | 4-Cl | H | $(CH_2)_4$ | 124.5–25.5 | 47.24 | 5.35 | 8.26 | 12.61 | 13.94 | 47.63 | 5.50 | 8.40 | 12.90 | 13.54 |

Exemplary of the preparation of the required primary amine starting materials is the following preparation of 4-(p-chlorophenyl)-butylamine:

A mixture of 4-(p-chlorophenyl)-butyric acid (6.7 g., 0.0337 mole) in 50 ml. of dry chloroform and 10 ml. (0.134 mole) of thionyl chloride was refluxed for 8 hours. Excess thionyl chloride was removed in vacuo and the residual oil was treated with toluene to remove traces of chloride. The residue was taken up in 10 ml. of toluene and added to 30 ml. of concentrated ammonium hydroxide in an ice-water bath to give 4-(p-chlorophenyl)-butyramide, m.p. 110°–113° C.

To a solution of 12.6 g. (0.33 mole) of lithium aluminum hydride in 340 ml. of dry ether was added dropwise at room temperature 16.4 g. (0.083 mole) of 4-(p-chlorophenyl)-butyramide. The reaction mixture was stirred at room temperature for 4 hours, cooled and cautiously quenched with 13 ml. of water, 10 ml. of 20% sodium hydroxide and 45 ml. of water. The organic layer was separated and the emulsion was extracted with ether. The combined organic and ether extract was dried over sodium hydroxide and concentrated to obtain 4-(p-chlorophenyl)butylamine; m.p. of hydrochloride salt 162°–164° C.

As a specific embodiment of a composition of this invention, an active ingredient such as 1,5-di-(4-phenylbutyl)-imidodisulfamide is dissolved in sterile water at a concentration of 0.5% and aerosolized from a nebulizer operating at an air flow adjusted to deliver the desired aerosolized weight of drug.

What is claimed is:

1. A compound represented by the formula:

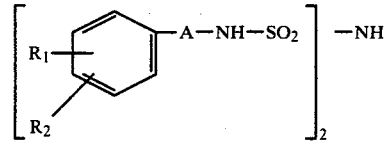

wherein:

A is a single valence bond, an alkylene chain $-(CH_2)_n-$ in which n is a positive integer 2, 3, 4 or 6, a branched alkylene chain of from 2 to 4 carbon atoms, or phenylmethylene;

$R_1$ is hydrogen, 3- or 4-bromo, 3- or 4-chloro, or 3- or 4-trifluoromethyl; and $R_2$ is hydrogen, with the proviso that when n is 2, $R_1$ is 4-chloro, 4-bromo, 4-methoxy or 3-trifluoromethyl and $R_2$ is hydrogen or together with $R_1$ in adjacent positions forms either a 3,4-dichloro substitution or a fused benzo ring, and further with the proviso that when A is a single valence bond $R_1$ is not hydrogen or 4-chloro, or an alkali metal salt of said compound.

2. A compound according to claim 1 in which A is an alkylene chain, $R_1$ is hydrogen, 3-bromo, 3-chloro or 4-chloro, and $R_2$ is hydrogen.

3. A compound according to claim 2 being the compound 1,5-di-(4-chlorophenethyl)-imidodisulfamide.

4. A compound according to claim 2 being the compound 1,5-di-(4-phenylbutyl)-imidodisulfamide.

5. A compound according to claim 1 in which A is a single valence bond.

6. A compound according to claim 5 being the compound 1,5-di-(4-bromophenyl)-imidodisulfamide.

7. A pharmaceutical composition for inhibiting the symptoms of asthma comprising a nontoxic pharmaceutical carrier or diluent and an amount sufficient to produce said inhibition of a compound of claim 1.

8. A pharmaceutical composition according to claim 7 in a form suitable for administration by inhalation.

9. A pharmaceutical composition according to claim 7 comprising a solution or suspension of the active ingredient in sterile water.

10. A pharmaceutical composition according to claim 7 in the form of an aerosol formulation.

11. A pharmaceutical composition according to claim 7 in which the pharmaceutical carrier or diluent is a solid.

12. A method of inhibiting the symptoms of asthma which comprises administering to an animal or human subject in need of said inhibition a therapeutically effective amount for producing said inhibition of a compound of claim 1.

13. The method according to claim 12 in which the active ingredient is administered in a daily dosage regimen of from about 0.5 mg. to about 2000 mg.

14. A method of antagonizing the effects of SRS-A on bronchial smooth muscle which comprises administering to an animal or human subject in need of said antagonism an amount sufficient to product said antagonism of a compound of claim 1.

* * * * *